(12) United States Patent
Robertson

(10) Patent No.: US 6,752,792 B1
(45) Date of Patent: Jun. 22, 2004

(54) VAGINAL CLEANING APPARATUS

(76) Inventor: Harold E. Robertson, 354 Claremont Ave., Mount Vernon, NY (US) 10552

( * ) Notice: Subject to any disclaimer, the term of this patent is extended or adjusted under 35 U.S.C. 154(b) by 0 days.

(21) Appl. No.: 09/939,032

(22) Filed: Aug. 24, 2001

(51) Int. Cl.⁷ ............................................. A61M 31/00
(52) U.S. Cl. .......................... 604/279; 604/35; 604/39; 4/443
(58) Field of Search ........................... 604/35, 39, 150, 604/246, 271, 279; 4/420.1, 420.4, 420.5, 443, 446

(56) References Cited

U.S. PATENT DOCUMENTS

| | | | |
|---|---|---|---|
| 3,914,804 A | * 10/1975 | Schrader et al. ............. 4/420.1 |
| 4,141,360 A | 2/1979 | Lasswell | |
| 4,178,931 A | * 12/1979 | Lind et al. .................. 604/151 |
| 4,371,993 A | * 2/1983 | Patrick .......................... 4/448 |
| 4,386,928 A | * 6/1983 | Hart ............................. 604/83 |
| 4,950,231 A | * 8/1990 | Liu ............................. 604/39 |
| 5,304,116 A | * 4/1994 | Cornelius ...................... 604/39 |
| 5,409,167 A | * 4/1995 | Borod ......................... 239/152 |
| D408,468 S | 4/1999 | Saka | |

* cited by examiner

*Primary Examiner*—Michael J. Hayes
*Assistant Examiner*—Kathryn Thompson

(57) ABSTRACT

A vaginal cleaning apparatus for increasing vaginal hygiene includes a housing having a top wall, a bottom wall and a peripheral wall. A container in the housing. An applicator has an upper wall, a lower wall and a perimeter wall. A first hole extends through the upper wall. A plurality of second holes is positioned around the first hole. A supply line has a first end fluidly coupled to the container and a second end is in fluid communication with the second holes. A drainage line has a first end and a second end. The first end of the drainage line is in fluid communication with the first hole in the upper wall. A supply pump is fluidly coupled to supply line. A drainage pump is fluidly coupled to the drainage line. Liquid pumped through the second holes may be drained through the first hole.

9 Claims, 3 Drawing Sheets

VAGINAL CLEANING APPARATUS

BACKGROUND OF THE INVENTION

1. Field of the Invention

The present invention relates to vaginal cleaning devices and more particularly pertains to a new vaginal cleaning apparatus for increasing vaginal hygiene.

2. Description of the Prior Art

The use of vaginal cleaning devices is known in the prior art. More specifically, vaginal cleaning devices heretofore devised and utilized are known to consist basically of familiar, expected and obvious structural configurations, notwithstanding the myriad designs encompassed by the crowded prior art which have been developed for the fulfillment of countless objectives and requirements.

Known prior art includes U.S. Pat. Nos. 4,178,931; 5,304,116; 4,141,360; 4,950,231; 4,386,928; and U.S. Des. Patent No. 408,468.

While these devices fulfill their respective, particular objectives and requirements, the aforementioned patents do not disclose a new vaginal cleaning apparatus. The inventive device includes a housing having a top wall, a bottom wall and a peripheral wall extending between the top and bottom wall such that an interior space is defined in the housing. A container is mounted in the interior space. The top wall has an opening therein extending into the container. An applicator has an upper wall, a lower wall and a perimeter wall extending between the upper and lower walls. A first hole extends through a generally central area of the upper wall. A plurality of second holes is positioned around the first hole. A supply line has a first end and a second end. The first end is fluidly coupled to the container. The second end extends upwardly through the top wall and is in fluid communication with the second holes. A drainage line has a first end and a second end. The first end of the drainage line is in fluid communication with the first hole in the upper wall. The second end of the drainage line extends through the lower wall of the applicator. A supply pump for pumping fluid through the supply line is positioned in the housing and is fluidly coupled to supply line. A drainage pump for draining fluid through the drainage line is positioned in the housing, the drainage pump is fluidly coupled to the drainage line. Liquid pumped through the second holes may be drained through the first hole. An actuator for selectively turning on the drainage and supply pumps is mounted on the top wall of the housing and is operationally coupled to the supply and drainage pumps. A power supply is operationally coupled to the actuator.

In these respects, the vaginal cleaning apparatus according to the present invention substantially departs from the conventional concepts and designs of the prior art, and in so doing provides an apparatus primarily developed for the purpose of increasing vaginal hygiene.

SUMMARY OF THE INVENTION

In view of the foregoing disadvantages inherent in the known types of vaginal cleaning devices now present in the prior art, the present invention provides a new vaginal cleaning apparatus construction wherein the same can be utilized for increasing vaginal hygiene.

The general purpose of the present invention, which will be described subsequently in greater detail, is to provide a new vaginal cleaning apparatus apparatus and method which has many of the advantages of the vaginal cleaning devices mentioned heretofore and many novel features that result in a new vaginal cleaning apparatus which is not anticipated, rendered obvious, suggested, or even implied by any of the prior art vaginal cleaning devices, either alone or in any combination thereof.

To attain this, the present invention generally comprises a housing having a top wall, a bottom wall and a peripheral wall extending between the top and bottom wall such that an interior space is defined in the housing. A container is mounted in the interior space. The top wall has an opening therein extending into the container. An applicator has an upper wall, a lower wall and a perimeter wall extending between the upper and lower walls. A first hole extends through a generally central area of the upper wall. A plurality of second holes is positioned around the first hole. A supply line has a first end and a second end. The first end is fluidly coupled to the container. The second end extends upwardly through the top wall and is in fluid communication with the second holes. A drainage line has a first end and a second end. The first end of the drainage line is in fluid communication with the first hole in the upper wall. The second end of the drainage line extends through the lower wall of the applicator. A supply pump for pumping fluid through the supply line is positioned in the housing and is fluidly coupled to supply line. A drainage pump for draining fluid through the drainage line is positioned in the housing, the drainage pump is fluidly coupled to the drainage line. Liquid pumped through the second holes may be drained through the first hole. An actuator for selectively turning on the drainage and supply pumps is mounted on the top wall of the housing and is operationally coupled to the supply and drainage pumps. A power supply is operationally coupled to the actuator.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new vaginal cleaning apparatus apparatus and method which has many of the advantages of the vaginal cleaning devices mentioned heretofore and many novel features that result in a new vaginal cleaning apparatus which is not anticipated, rendered obvious, suggested, or even implied by any of the prior art vaginal cleaning devices, either alone or in any combination thereof.

It is another object of the present invention to provide a new vaginal cleaning apparatus which may be easily and efficiently manufactured and marketed.

It is a further object of the present invention to provide a new vaginal cleaning apparatus which is of a durable and reliable construction.

An even further object of the present invention is to provide a new vaginal cleaning apparatus which is susceptible of a low cost of manufacture with regard to both materials and labor, and which accordingly is then susceptible of low prices of sale to the consuming public, thereby making such vaginal cleaning apparatus economically available to the buying public.

Still yet another object of the present invention is to provide a new vaginal cleaning apparatus which provides in the apparatuses and methods of the prior art some of the advantages thereof, while simultaneously overcoming some of the disadvantages normally associated therewith.

Still another object of the present invention is to provide a new vaginal cleaning apparatus for increasing vaginal hygiene.

Yet another object of the present invention is to provide a new vaginal cleaning apparatus which includes a housing having a top wall, a bottom wall and a peripheral wall extending between the top and bottom wall such that an interior space is defined in the housing. A container is mounted in the interior space. The top wall has an opening therein extending into the container. An applicator has an upper wall, a lower wall and a perimeter wall extending between the upper and lower walls. A first hole extends through a generally central area of the upper wall. A plurality of second holes is positioned around the first hole. A supply line has a first end and a second end. The first end is fluidly coupled to the container. The second end extends upwardly through the top wall and is in fluid communication with the second holes. A drainage line has a first end and a second end. The first end of the drainage line is in fluid communication with the first hole in the upper wall. The second end of the drainage line extends through the lower wall of the applicator. A supply pump for pumping fluid through the supply line is positioned in the housing and is fluidly coupled to supply line. A drainage pump for draining fluid through the drainage line is positioned in the housing, the drainage pump is fluidly coupled to the drainage line. Liquid pumped through the second holes may be drained through the first hole. An actuator for selectively turning on the drainage and supply pumps is mounted on the top wall of the housing and is operationally coupled to the supply and drainage pumps. A power supply is operationally coupled to the actuator.

Still yet another object of the present invention is to provide a new vaginal cleaning apparatus that FOCUSED1.

Even still another object of the present invention is to provide a new vaginal cleaning apparatus that FOCUSED2.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
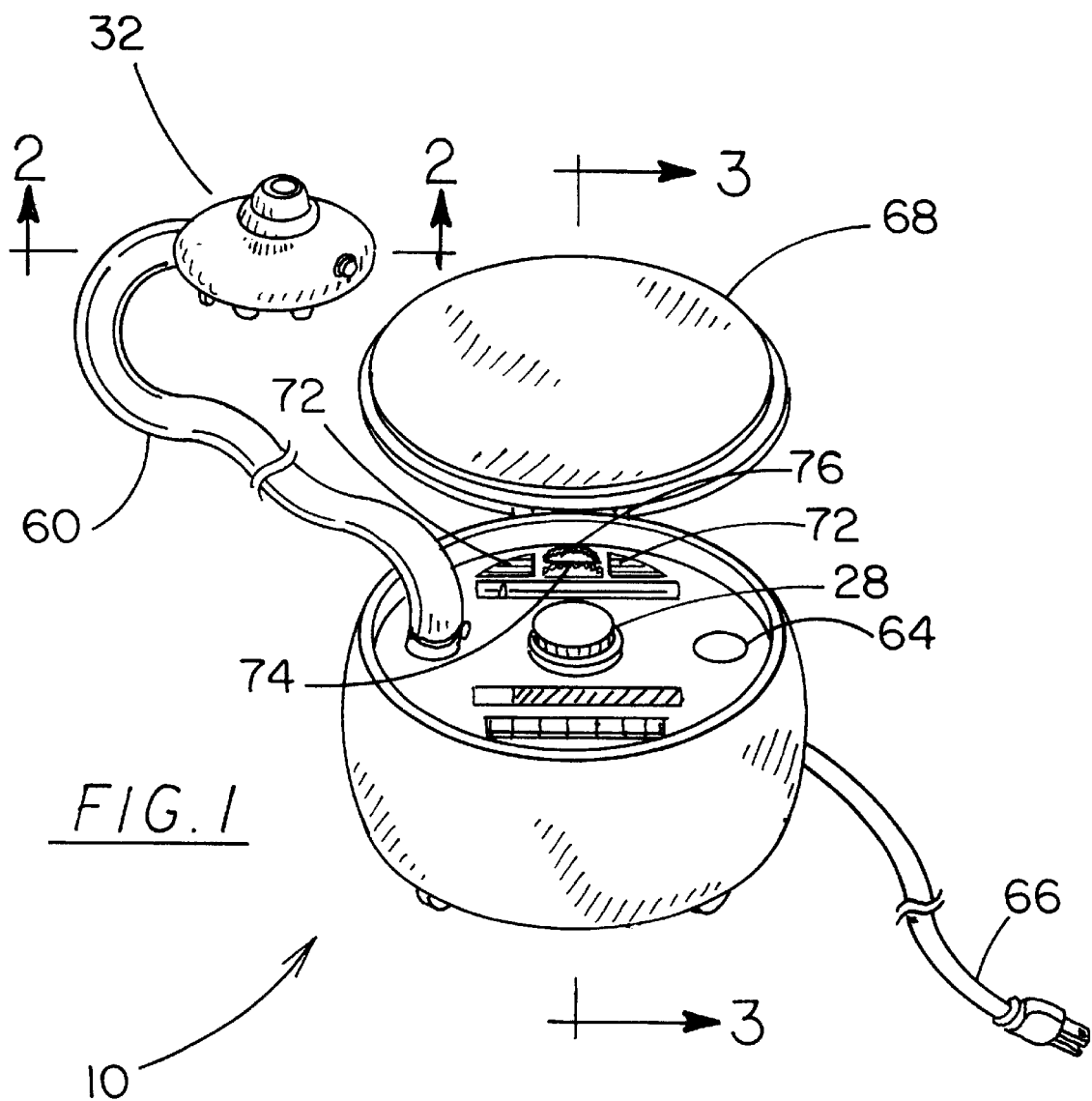
FIG. 1 is a schematic perspective view of a new vaginal cleaning apparatus according to the present invention.
Figure 2:
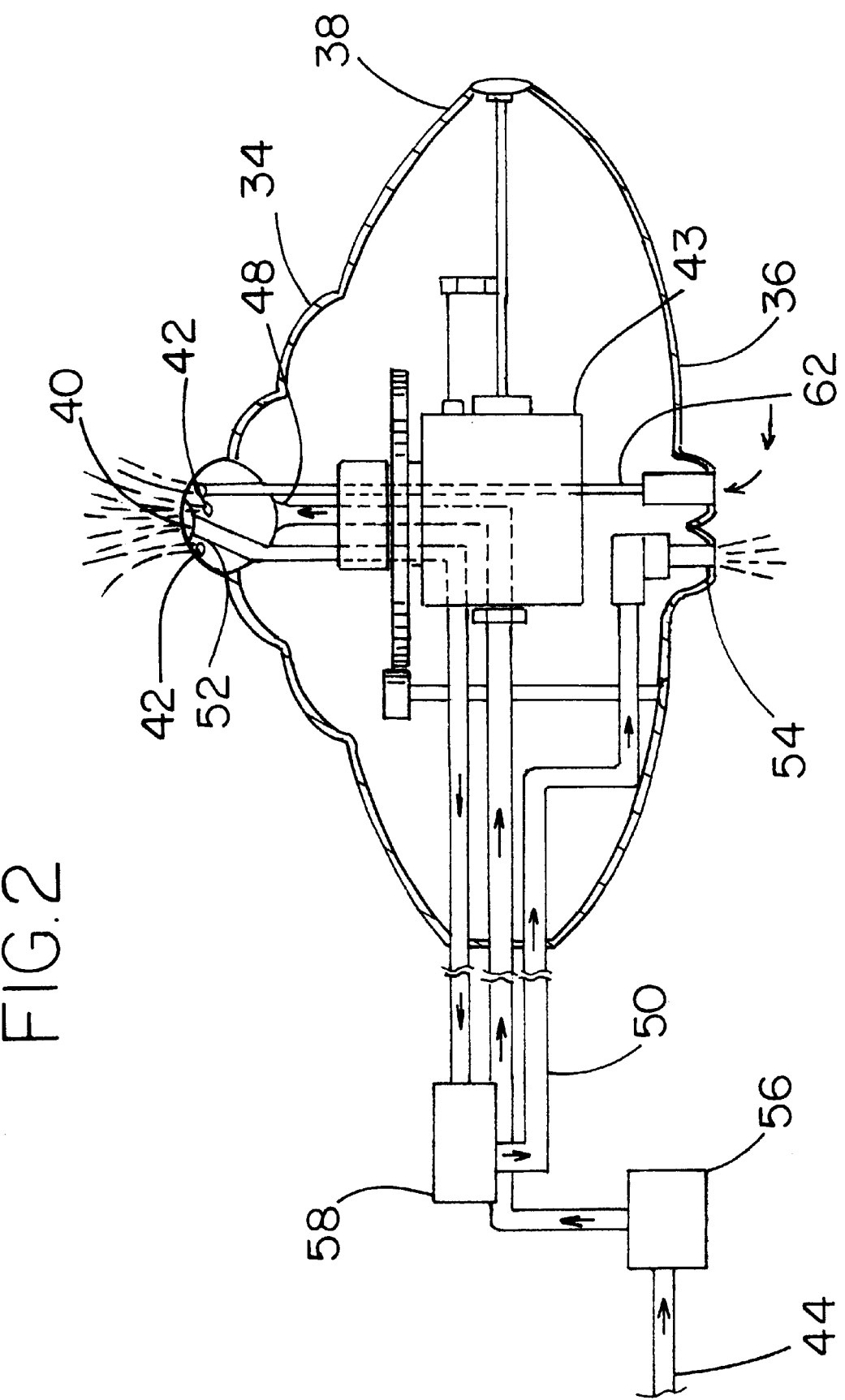
FIG. 2 is a schematic cross-sectional view of the applicator along line 2—2 of FIG. 1 of the present invention.
Figure 3:
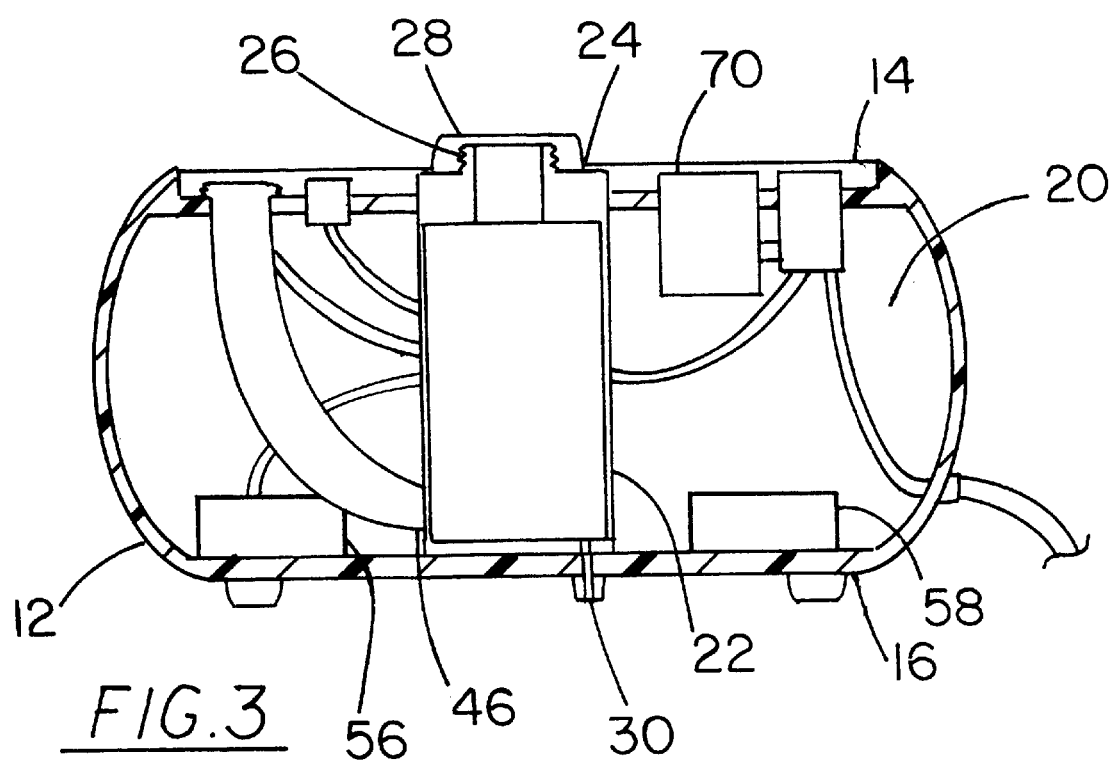
FIG. 3 is a schematic cross-sectional view taken along line 3—3 of the present invention.

With reference now to the drawings, and in particular to FIGS. 1 through 3 thereof, a new vaginal cleaning apparatus embodying the principles and concepts of the present invention and generally designated by the reference numeral 10 will be described.

As best illustrated in FIGS. 1 through 3, the vaginal cleaning apparatus 10 generally comprises a housing 12 having a top wall 14, a bottom wall 16 and a peripheral wall 18 extending between the top 14 and bottom 16 walls such that an interior space 20 is defined in the housing 12. A container 22 is mounted in the interior space 20. The top wall 14 has an opening 24 therein extending into the container 22. An annular lip 26 extends upwardly from an edge of the opening 24. The annular lip 26 is threaded. A cap 28 is positionable on and threadably coupled to the annular lip 26. Ideally, a drainage hole 30 extends through the bottom wall 16 and into the container 22.

An applicator 32 has an upper wall 34, a lower wall 36 and a perimeter wall 38 extending between the upper 34 and lower 36 walls. The upper wall 34 is dome-shaped and extends upwardly away from the lower wall 36. A first hole 40 extends through a generally central area of the upper wall 34. A plurality of second holes 42 is positioned around the first hole 40. A valve 43 is positioned in the applicator 32.

A supply line 44 has a first end 46 and a second end 48. The first end 46 is fluidly coupled to the container 22. The second end 48 extends upwardly through the top wall 14. The supply line 44 is secured to the top wall. The second end 48 of the supply line 44 is in fluid communication with the second holes 42. The valve 43 is adapted for selectively opening and closing the supply line 44.

A drainage line 50 has a first end 52 and a second end 54. The first end 52 of the drainage line 50 is in fluid communication with the first hole 40 in the upper wall 34. The second end 54 of the drainage line 50 extends through the lower wall 36 of the applicator 32.

A supply pump 56 for pumping fluid through the supply line 44 is positioned in the housing 12 and is fluidly coupled to supply line 44. A drainage pump 58 for draining fluid through the drainage line 50 is positioned in the housing 12. The drainage pump 58 is fluidly coupled to the drainage line 50. Each of the supply 44 and drainage 50 lines extends through the perimeter wall 38 of the applicator 32. A sheath 60 extends between the applicator 32 and the housing 12 and generally covers portions of the supply 44 and drainage 50 lines extending between the housing 12 and the applicator 32. Liquid pumped through the second holes 42 may be drained through the first hole 40.

An air intake line 62 extends between the upper wall 34 and the lower wall 36 and extends through the applicator 32. The air intake line 62 prevents a vacuum from being created when the valve closes 43 the supply line 44. Air may travel from the air intake line 62, through the upper wall 34 and into the drainage line 50.

An actuator 64 for selectively turning on the drainage 58 and supply 56 pumps and is mounted on the top wall 14 of the housing 12 and is operationally coupled to the supply 56 and drainage 58 pumps. A power supply 66 is operationally coupled to the actuator 64. The power supply 66 preferably includes a power cord.

A cover 68 is hingedly coupled to an upper edge of the peripheral wall 18 of the housing 12. The cover 68 is positionable over the top wall 14 of the housing 12. Ideally, a space is defined between the cover 68 and the top wall 14 when the cover 68 is in a closed position. The applicator 32 is then positionable in the space for storage.

A generally conventional radio 70 is preferably mounted in the top wall 14 of the housing 12. A plurality of speakers 72 for emitting audible sounds is mounted to the top wall 14 and is operationally coupled to the radio 70. A frequency selector 74 is operationally coupled to the radio. A volume control 76 is operationally coupled to the radio. The radio 70 is operationally coupled to the power supply.

In use, the user may fill the container 22 with a cleansing solution of their choice. The pumps 56, 58 are turned on which sends liquid out through the second holes 42 of the applicator 32. The applicator 32 is placed adjacent to the vagina for applying the liquid to the vagina. The liquid is drawn through the first hole 40 and is sent outward through the lower wall 36 of the applicator 32. The radio 70 provides background sound to offer more privacy for the user of the device 10.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A vaginal cleaning device comprising:

a housing having a top wall, a bottom wall and a peripheral wall extending between said top and bottom wall such that an interior space is defined in said housing, a container being mounted in said interior space, said top wall having an opening therein extending into said container;

an applicator having an upper wall, a lower wall and a perimeter wall extending between said upper and lower walls, a first hole extending through a generally central area of said upper wall, a plurality of second holes being positioned around said first hole;

a supply line having a first end and a second end, said first end being fluidly coupled to said container, said second end extending upwardly through said top wall and being in fluid communication with said second holes;

a drainage line having a first end and a second end, said first end of said drainage line being in fluid communication with said first hole in said upper wall, said second end of said drainage line extending through said lower wall of said applicator;

a supply pump for pumping fluid through said supply line being positioned in said housing and being fluidly coupled to supply line;

a drainage pump for draining fluid through said drainage line being positioned in said housing, said drainage pump being fluidly coupled to said drainage line, each of said supply and drainage lines extending through said perimeter wall of said applicator, wherein liquid pumped through said second holes may be drained through said first hole;

an actuator for selectively turning on said drainage and supply pumps being mounted on said top wall of said housing and being operationally coupled to said supply and drainage pumps; and a power supply being operationally coupled to said actuator.

2. The vaginal cleaning device as in claim 1, further including an annular lip extending upwardly from an edge of said opening, said annular lip being threaded, a cap being positionable on and threadably coupled to said annular lip.

3. The vaginal cleaning device as in claim 1, wherein said upper wall of said applicator is dome-shaped and extends upwardly away from said lower wall.

4. The vaginal cleaning device as in claim 1, further including a valve being positioned in said applicator, said valve being adapted for selectively opening and closing said supply line.

5. The vaginal cleaning device as in claim 1, wherein each of said supply and drainage lines extend through said perimeter wall of said applicator, a sheath extends between said applicator and said housing and generally covering portions of said supply and drainage lines extending between said housing and said applicator.

6. The vaginal cleaning device as in claim 1, further including an air intake line extending between said upper wall and said lower wall and extending through said applicator.

7. The vaginal cleaning device as in claim 1, further including a cover being hingedly coupled to an upper edge of said peripheral wall of said housing, said cover being positionable over said top wall of said housing, wherein a space is defined between said cover and said top wall when said cover is in a closed position, said applicator being positioned in said space.

8. The vaginal cleaning device as in claim 1, further including a radio being mounted in said top wall of said housing, a plurality of speakers for emitting audible sounds being mounted in said top wall and being operationally coupled to said radio, a frequency selector being operationally coupled to said radio, a volume control being operationally coupled to said radio.

9. A vaginal cleaning device comprising:

a housing having a top wall, a bottom wall and a peripheral wall extending between said top and bottom wall such that an interior space is defined in said housing, a container being mounted in said interior space, said top wall having an opening therein extending into said container, an annular lip extending upwardly from an edge of said opening, said annular lip being threaded, a cap being positionable on and threadably coupled to said annular lip;

an applicator having an upper wall, a lower wall and a perimeter wall extending between said upper and lower walls, said upper wall being dome-shaped and extending upwardly away from said lower wall, a first hole extending through a generally central area of said upper wall, a plurality of second holes being positioned around said first hole, a valve being positioned in said applicator;

a supply line having a first end and a second end, said first end being fluidly coupled to said container, said second end extending upwardly through said top wall, said supply line being secured to said top wall, said second end of said supply line being in fluid communication with said second holes, said valve being adapted for selectively opening and closing said supply line;

a drainage line having a first end and a second end, said first end of said drainage line being in fluid communication with said first hole in said upper wall, said second end of said drainage line extending through said lower wall of said applicator;

a supply pump for pumping fluid through said supply line being positioned in said housing and being fluidly coupled to supply line;

a drainage pump for draining fluid through said drainage line being positioned in said housing, said drainage pump being fluidly coupled to said drainage line, each of said supply and drainage lines extending through said perimeter wall of said applicator, a sheath extending between said applicator and said housing and generally covering portions of said supply and drainage lines extending between said housing and said applicator, wherein liquid pumped through said second holes may be drained through said first hole;

an air intake line extending between said upper wall and said lower wall and extending through said applicator;

an actuator for selectively turning on said drainage and supply pumps being mounted on said top wall of said housing and being operationally coupled to said supply and drainage pumps;

a power supply being operationally coupled to said actuator, said power supply including a power cord;

a cover being hingedly coupled to an upper edge of said peripheral wall of said housing, said cover being positionable over said top wall of said housing; and a radio being mounted in said top wall of said housing, a plurality of speakers for emitting audible sounds being mounted in said top wall and being operationally coupled to said radio, a frequency selector being operationally coupled to said radio, a volume control being operationally coupled to said radio, said radio being operationally coupled to said power supply.

* * * * *